United States Patent [19]

Berman et al.

[11] Patent Number: 5,013,759

[45] Date of Patent: May 7, 1991

[54] COMPOUNDS AND COMPOSITIONS HAVING ANTI-INFLAMMATORY AND ANALGESIC ACTIVITY

[75] Inventors: Elizabeth F. Berman, Cincinnati, Ohio; Brian L. Buckwalter, Yardley, Pa.; Thomas L. Cupps, Oxford; Joseph H. Gardner, Cincinnati, both of Ohio

[73] Assignee: The Procter & Gamble Company, Cincinnati, Ohio

[21] Appl. No.: 473,122

[22] Filed: Jan. 31, 1990

Related U.S. Application Data

[63] Continuation of Ser. No. 220,355, Jul. 14, 1988, abandoned, which is a continuation of Ser. No. 90,418, Aug. 27, 1987, abandoned, which is a continuation of Ser. No. 742,833, Jun. 10, 1985, abandoned.

[51] Int. Cl.$^5$ .......................................... A61K 31/165
[52] U.S. Cl. ..................................... 514/622; 564/170; 564/74
[58] Field of Search .................. 564/74, 170; 514/622

[56] References Cited

U.S. PATENT DOCUMENTS

| | | | |
|---|---|---|---|
| 3,268,582 | 8/1966 | Zeile et al. | 424/324 |
| 3,621,043 | 11/1971 | Seki . | |
| 4,075,132 | 2/1978 | Portlock | 546/74 |
| 4,238,505 | 12/1980 | Engel | 560/124 |
| 4,238,524 | 12/1980 | Nelson | 424/324 |
| 4,313,958 | 2/1982 | LaHann | 514/627 |
| 4,401,663 | 8/1983 | Buckwalter et al. | 564/99 X |
| 4,424,205 | 1/1984 | LaHann et al. | 564/170 X |
| 4,443,473 | 4/1984 | Buckwalter et al. | 560/29 X |
| 4,460,602 | 7/1984 | Buckwalter et al. | 564/63 X |
| 4,493,848 | 1/1985 | LaHann et al. | 424/324 |
| 4,496,762 | 1/1985 | Kashdan | 564/170 |
| 4,532,139 | 7/1985 | Janusz et al. | 564/74 |

FOREIGN PATENT DOCUMENTS

| | | |
|---|---|---|
| 626897 | 5/1963 | Belgium . |
| 54174 | 6/1982 | European Pat. Off. . |
| 2818995 | 11/1978 | Fed. Rep. of Germany . |
| 1336388 | 8/1963 | France . |

OTHER PUBLICATIONS

Chem. Abs. 100:174451w corresponding to Japanese Kokai 58/203,939.
Chem. Abs. 99:70584m corr. to Spanish Patent 505,866.
Chem. Abs. 90:123228w corr. to Japanese Kokai 78/124,600.
Derwent Abs. 91760 corr. to Jap. Kokai 81/139,413.
Derwent Abs. 95904 corr. to Jap. Kokai 81/147,752.
Ferris et al., "New Approach to Insecticidal Paints", Aust. Commonwealth Dept. Supply Def. Stand. Lab Tech., Note No. 89 (1966) (Chem. Abs. 67:22919s).
Kiernan, "A Study of Chemically Induced Acute Inflammation in the Skin of the Rat", Quart. J. Exp. Physiol., vol. 62, (1977) pp. 151-161.
Jansco et al., "Direct Evidence of Neurogenic Inflammation and Its Prevention by Denervation and by Pretreatment with Capsaicin," Br. J. Pharm. Chemother. vol. 3 (1967), pp. 138-151.
Arvier et al., "Modification by Capsaicin and Compound 48/80 of Dye Leakage Induced by Irritants in the Rat," Br. J. Pharm., vol. 59 (1977), pp. 61-68.
Yaksh et al., "Intrathecal Capsaicin Depletes Substance P in the Rat Spinal Cord and Produces Prolonged Thermal Analgesia," Science, vol. 206 (1979), pp. 481-483.
Virus et al., "Pharmacologic Actions of Capsaicin: Apparent Involvement of Substance P and Serotonin", Life Sciences, vol. 25 (1979), pp. 1273-1281.
Jones et al., "The Relation Between Chemical Constitution and Pungency in Acid Amides," J. Chem. Soc., vol. 127 (1925), pp. 2588-2598.
Newman, "Natural and Synthetic Pepper-Flavored Substances", Chem. Prod., (Mar. 1954), 102-106.
Szolesanyi et al., "Sensory Effects of Capsaicin Congeners," Arzneim.-Forsch., vol. 25 (1975), pp. 1871-1881.
Szolesanyi et al., "Sensory Effects of Capsaicin Congeners," Arzneim.-Forsch., vol. 26 (1976), pp. 33-37.
Hegyes et al., "Synthesis of Homovanillic Acid Derivatives of Capsaicin-Like Effect," Acta. Phys. Chem. vol. 20 (1974), pp. 115-120.
Michalska et al., "Synthesis and Local Anesthetic Properties of N-substituted 3,4-Dimethoxyphenethylamine Derivatives," Dep. Pharm. Pharmacol., vol. 24 (1972), pp. 17-25 (Chem. Abs. 77: 19271a).
T. Szeki, "Contributions Towards Understanding the Relation Between the Chemical Constitution and the Sharp Taste of Acylamines," Arch. Pharm., vol. 268, (1930), pp. 151-157.
Ott et al., Liebigs Ann. vol. 425 (1921), pp. 314-337.
Nelson, "Vanillyl-acyl Amides", J. Am. Chem. Soc. vol. XLI (1919), pp. 2121-2130.

(List continued on next page.)

Primary Examiner—Carolyn S. Elmore
Attorney, Agent, or Firm—Milton B. Graff, IV; David K. Dabbiere; Steven J. Goldstein

[57] ABSTRACT

Substituted phenylacetic acid amide compounds, and pharmaceutically-acceptable salts thereof, of the formula:

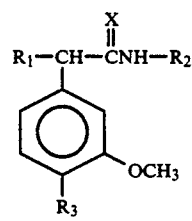

wherein X is O or S; $R_1$ is H, OH or $CH_3$; $R_2$ is straight chain alkenyl, branched chain or cyclic hydrocarbon having from about 7 to about 24 carbon atoms; $R_3$ is OH, $OSO_3^-$, $OPO_3^{--}$ or a short chain ester with from about 1 to about 6 carbon atoms.

15 Claims, No Drawings

OTHER PUBLICATIONS

Casalini et al., "Metabolites and Analogs of 2-Ethyl-2,-3-Dihydro-5-Benzofuranacetic acid (Furofenac): Chemical and Pharmacological Properties", J. Pharm. Sci., vol. 69 (1980), pp. 164-167 (Chem. Abs. 93:60886y).

Narasimhachari et al., "Simultaneous Determination by GC-MS-SIM of o-, m-, p-Hydroxy Phenylacetic Acid, 3,4-Dihydroxy Phenylacetic Acid in Biological Samples Using a Common Selected Ion", *J. Chromatogr. Sci.*, vol. 16 (1978), pp. 263-267.

Bodor et al., "Soft Drugs, VI. The Application of the Inactive Metabolite Approach for Design of Soft Beta-Blockers", *Pharm. Res.* vol. 3 (1984), pp. 120-125, (Chem. Abs. 101: 204164v).

Jansco et al., "Sensory Neurotoxins: Chemically Induced Selective Destruction of Primary Sensory Neurons", Brain Res. vol. 210 (1981), pp. 83-89, (Chem. Abs. 94: 185577a).

COMPOUNDS AND COMPOSITIONS HAVING ANTI-INFLAMMATORY AND ANALGESIC ACTIVITY

This application is a continuation of 07/220,355, filed Jul. 14, 1988, which is a continuation of 07/090,418, filed Aug. 27, 1987, which is a continuation of 06/742,833, filed Jun. 10, 1985, all abandoned.

TECHNICAL FIELD

The present invention relates to certain substituted phenylacetic acid amides and pharmaceutical compositions containing these compounds which exhibit anti-inflammatory and analgesic activity.

BACKGROUND OF THE INVENTION

Inflammation, or the "inflammatory response", is the result of complex interconnected physiological events, including increased vascular permeability, fluid accumulations, and the migration of a changing population of inflammatory cells into the inflamed area. The clinical manifestations of inflammation include swelling (edema), increased local temperature, erythema, and pain. The inflammatory response can be triggered by any of a number of causative factors, including certain bacteria, radiation, hypersensitivity to chemical agents, arthritis-like conditions, and the like. The inflammatory response is generally believed to be a primary defense mechanism in the body, but, unchecked, can become excessive and can result in functional impairment.

The use of non-steroidal anti-inflammatory, antipyretic and analgesic drugs, especially the salicylates, which include aspirin and aspirin derivatives, to combat inflammation and attendant pain is accepted medical practice. The non-steroidals are commonly employed to relieve pain and inflammation associated with, for example, bursitis, arthritis, and the like.

While pain is incapable of precise definition due to its basically subjective nature, it can generally be said that the term refers to feelings of distress or suffering caused by stimulation of specialized nerve endings. A great variety of drugs have been developed to reduce pain in man and other animals; some directed to eliminating pain at its source, and others directed to blocking the assimilation of pain by the brain. Among the latter group of drugs that are designed to block the sensation of pain, are the analgesics, which generally relieve pain without causing unconsciousness. Analgesics can be further classified in two main categories: opioid analgesics, including morphine, codeine, levorphanol, and the morphine-like analgesics meperidine, and methadone; and antipyretic analgesics, such as aspirin, ibuprofen, phenacetin, acetaminophen, phenylbutazone, and indomethacin.

Although the precise pharmacological action of these analgesics is uncertain, there are certain effects which readily distinguish the opioid analgesics from the antipyretics. In particular, the antipyretics are weak analgesics, with much of their effect in the peripheral nervous system, so that behavioral changes do not usually occur. Generally, these analgesics relieve only somatic pain originating from muscles, joints, tendons and fasciae, and are ineffective against deep visceral pain. However, the opioid analgesics are quite effective against all types of pain, with broad-based action in the central nervous system. Aside from potent analgesia, the opioids, also known as narcotics, often produce effects on mood and other behavioral changes. Perhaps the most notable side effect of the opioid analgesics is the fact that their repeated use is associated with tolerance, as well as psychic and physical dependence.

It has been recently discovered that capsaicin, a natural product of certain species of the genus Capsicium, induces analgesia. Capsaicin (trans-8-methyl-N-vanillyl-6-nonenanamide) and "synthetic" capsaicin (N-vanillylnonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al, *Science*, 206, pp 481-483 (1979); Jancso, et al, *Naunyn-Schmiedeberg's Arch. Pharmacol.*, Vol. 311, pp 285-288 (1980) and Holzer et al, *Eur. J. Pharm.* Vol. 58, pp 511-514 (1979). U.S. Pat. No. 4,238,505, Nelson, issued Dec. 9, 1980, discloses 3-hydroxyacetanilide for use in producing analgesia in animals. European Patent Application No. 0089710, LaHann, et al, published Sept. 28, 1983, describes hydroxyphenylacetamides with analgesic and anti-irritant activity. Similarly, analgesic and anti-irritant activity is disclosed for N-vanillyl sulfonamides in U.S. Pat. No. 4,401,663, Buckwalter, et al, issued Aug. 30, 1983; hydroxyphenyl-acetamides in U.S. Pat. No. 4,424,205, LaHann, et al, issued Jan. 31, 1984; N-(3- or 4- hydroxy or 3,4-dihydroxybenzyl) carbamates in U.S. Pat. No. 4,443,473, Buckwalter, et al, issued Apr. 17, 1984; N-[(substituted phenyl) methyl]-cis-monounsaturated alkenamides in U.S. Pat. No. 4,493,848, LaHann, et al, issued Jan. 15, 1985; N-(3-methoxy-4-hydroxybenzyl and phenyl) ureas and thioureas in U.S. Pat. No. 4,460,602, Buckwalter, et al, issued Jul. 17, 1984; N-vanillylureas in European Patent Application No. 0068590, Buckwalter, et al, published Jan. 5, 1983; N-[(substituted phenyl)methyl] alkynamides in U.S. patent application Ser. No. 514,204, Janusz, et al, filed Jul. 14, 1983; methylene substituted N-[(substituted phenyl)methyl] alkanamides in U.S. patent application Ser. No. 514,205, Janusz, et al, filed Jul. 14, 1983; N-[(substituted phenyl) methyl]-diunsaturated amides in U.S. patent application Ser. No. 514,207, LaHann, et al, filed Jul. 14, 1983; monoalkenamides in U.S. patent application Ser. No. 676,025, LaHann, et al, filed Nov. 28, 1984; trienamides in U.S. patent application Ser. No. 684,427, Janusz, et al, filed Dec. 20, 1984; substituted phenylacetic acid esters in U.S. patent application Ser. No. 684,428, Loomans, et al, filed Dec. 20, 1984; N-(substituted alkyl)alkanamides and thioamides in U.S. patent application Ser. No. 684,429, Loomans, et al, filed Dec. 20, 1984; substituted aromatic-araalkanamides in U.S. patent application Ser. No. 684,430, Janusz et al, filed Dec. 20, 1984; and combinations of capsaicinoids and arylalkanoic acids in U.S. patent application Ser. No. 684,642, Brand, filed Dec. 24, 1984.

It has now been discovered that certain substituted phenylacetic acid amides have anti-inflammatory and analgesic activity in humans and lower animals. Some of these substituted phenylacetic acid amide compounds have analgesic potency far greater than that of aspirin and comparable to that of the opioids, but do not exhibit undesirable narcotic side effects such as tolerance and physical dependence. These substituted phenylacetic acid amide compounds are also less toxic than capsaicin.

U.S. Pat. No. 4,493,848 discloses analgesic compounds, many of which are reverse amides of the compounds of the present invention. Surprisingly, however, the compounds of the present invention notwithstanding their close structural similarity to the compounds described in the aforementioned U.S. Patent, demonstrate greatly enhanced analgesic efficacy when taken orally. Additionally, for capsaicinoids of the prior art, it has been found that the "cis" (or Z) stereoisomers have an analgesic activity significantly greater than that of their "trans" (or E) isomers. Surprisingly, the cis and trans isomers of the substituted phenylacetic acid amide compounds of the present invention are approximately equipotent exhibiting strong analgesic activity.

The "cis" prefix is used in designating geometrical isomers in which there is a double bond between two carbon atoms and wherein the primary substituent group for each of the two carbon atoms is on the same side of the double bond axis. Conversely, the "trans" isomer designates a spatial arrangement wherein the primary substituent groups on each of the two carbon atoms in the double bond are on opposite sides of the bond axis.

SUMMARY OF THE INVENTION

The present invention provides compounds useful for relieving inflammation and producing analgesia in humans and lower animals, of the formula:

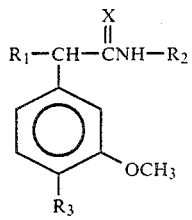

wherein X is O or S; $R_1$ is H, OH or $CH_3$; $R_2$ is straight chain alkenyl or branched chain or cyclic hydrocarbon having from 7 to 24 carbon atoms; $R_3$ is OH, $OSO_3^-$, $OPO_3^{--}$ or short chain ester with from 1 to about 6 carbon atoms; and pharmaceutically acceptable salts thereof.

This invention also provides pharmaceutical compositions comprising a safe and effective amount of these compounds and a pharmaceutically-acceptable carrier. Also provided are methods for producing analgesia and reducing inflammation by administering the compounds and compositions of this invention.

DETAILED DESCRIPTION OF THE INVENTION

The compositions and methods of this invention incorporate certain substituted phenylacetic acid amides or pharmaceutically acceptable salts thereof, of the formula:

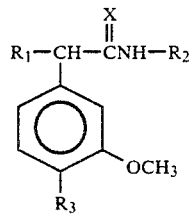

wherein X is O or S, preferably O; $R_1$ is H, OH, or $CH_3$, preferably H or $CH_3$; $R_2$ is straight chain alkenyl, or a branched chain or cyclic hydrocarbon having from about 7 to about 24 carbon atoms, preferably a straight chain alkenyl or branched chain hydrocarbon having from about 7 to about 20 carbon atoms and most preferably 14 to 20 carbon atoms; $R_3$ is OH, $OSO_3^-$, $OPO_3^{--}$ or a short chain ester with 1 to 6 carbon atoms and preferably is OH.

Preferred substituted phenylacetic acid amides include those wherein $R_2$ is derived from such monounsaturated fatty amines as 9E- or 9Z-tetradecenylamine, 9E- or 9Z-hexadecenylamine, 9E- or 9Z-octadecenylamine, 6E- or 6Z-octadecenylamine, 11E- or 11Z-octadecenylamine, 10E- or 10Z-nonadecenylamine, 13E- or 13Z-docosenylamine and 9-methylene-1-octadecanylamine. A particularly preferred substituted phenylacetic acid amide is N-oleyl-(4-hydroxy-3-methoxyphenyl)acetamide. Preferred pharmaceutically-acceptable substituted phenylacetic acid amide salts include the sodium, potassium, calcium, magnesium, and ammonium salts.

The substituted phenylacetic acid amides described herein can be readily prepared by the following general synthetic scheme:

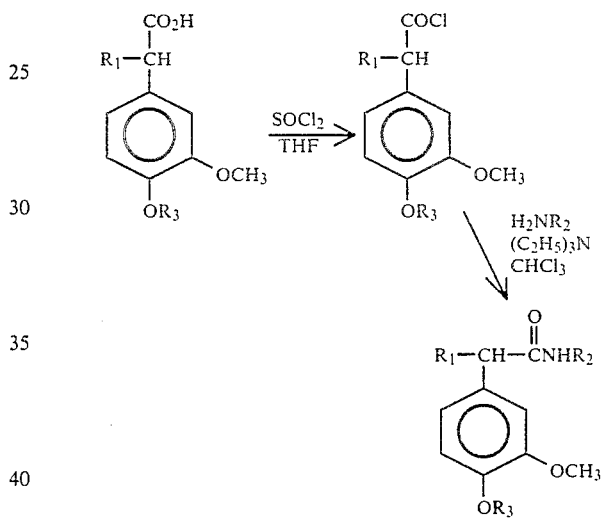

The amide is converted to the corresponding thioamide by treatment with 2,4-bis (4-methoxyphenyl)-1,3-dithia-2,4-diphosphetane-2,4-disulfide (Lawesson's reagent):

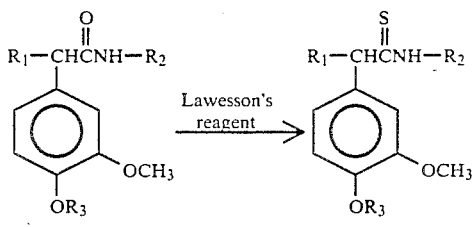

The fatty amines used in the synthesis of the preferred substituted phenylacetic acid amides are commercially available or are readily synthesized using techniques well known in the art.

COMPOSITIONS

The compositions of the present invention comprise:
(a) a safe and effective amount of a substituted phenylacetic acid amide of the present invention of mixtures thereof; and
(b) a pharmaceutically-acceptable carrier.

A safe and effective amount of substituted phenylacetic acid amide is that amount which provides analgesia, thereby alleviating or preventing the pain being treated at a reasonable benefit/risk ratio, as is attendant with any medical treatment. The substituted phenylacetic acid amides can also be used in combinations with other known analgesics and anti-pyretics. Such combinations can include safe and effective amounts of the substituted phenylacetic acid amides admixed with safe and effective amounts of the other agent, for example codeine, Tylenol or aspirin. Obviously, the amount of the substituted phenylacetic acid amide or the mixture which is administered will vary with such factors as the particular condition that is being treated, the severity of the condition that is being treated, the duration of the treatment, the physical condition of the patient, the nature of concurrent therapy (if any), the specific formulation and carrier employed, and the solubility and concentration of substituted phenylacetic acid amide or mixture used.

Various oral dosage forms can be used, including such solid forms as tablets, capsules, granules, bulk powders and microcapsules of the drug. These oral forms comprise a safe and effective amount, usually at least about 5%, and preferably from about 25% to about 50% of the substituted phenylacetic acid amide. Tablets can be compressed, enteric-coated, sugar-coated or film-coated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin, propylene glycol, ethyl oleate, cottonseed oil and sesame oil. Specific examples of pharmaceutically-acceptable carriers and excipients that may be used in formulating oral dosage forms containing substituted phenylacetic acid amides, are described in U.S. Pat. No. 3,903,297, Robert, issued Sept. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated herein by reference. Techniques and compositions for making tablets (compressed, formulas and molded), capsules (hard and soft gelatin) and pills are described in *Remington's Pharmaceutical Sciences* (Arthur Osol, editor), 1553–1593 (1980), incorporated herein by reference.

The compositions of the present invention can also be administered topically to a biological subject, i.e., by the direct laying on or spreading of the composition on epidermal or epithelial tissue. Such compositions include lotions, creams, solutions, gels and solids. These topical compositions comprise a safe and effective amount, usually at least about 0.5%, and preferably from about 1% to about 5%, of the substituted phenylacetic acid amide. Suitable carriers for topical administration of the substituted phenylacetic acid amide preferably remain in place on the skin as a continuous film and resist being washed off easily by perspiration or by immersion in water. Generally, the carrier is either organic in nature or an aqueous emulsion and capable of having the substituted phenylacetic acid amide dispersed or dissolved therein. The carrier may include pharmaceutically-acceptable emollients, skin penetration enhancers, coloring agents, fragrances, emulsifiers, thickening agents, and solvents. A more detailed description of such forms follows:

1. Lotions

The lotions can comprise an effective amount of the substituted phenylacetic acid amide; from 1% to 25%, preferably from 3% to 15%, of an emollient; the balance being water, a $C_2$ or $C_3$ alcohol, or a mixture of water and the alcohol. Several emollients are known. Examples of such emollients are as follows:

1. Hydrocarbon oils and waxes. Examples are mineral oil, petrolatum, paraffin, ceresin, ozokerite, microcrystalline wax, polyethylene, and perhydrosqualene.

2. Silicone oils, such as dimethylpolysiloxanes, methylphenylpolysiloxanes, water-soluble and alcohol-soluble silcone-glycol copolymers.

3. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 9 to 22 carbon atoms. Suitable examples include pelargonic, lauric, myristic, palmitic, stearic, isostearic, hydroxystearic, oleic, linoleic, ricinoleic, arachidonic, behenic, and erucic acids.

9. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550, 750, 2000, 5000, poly[ethylene oxide] homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivates of trimethylolpropane are examples thereof.

14. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters such as beeswax, spermaceti, myristyl myristate, stearyl stearate.

16. Beeswax derivatives, e.g., polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids such as lecithin and derivatives.

19. Sterols. Cholesterol, cholesterol fatty acid esters are examples thereof.

20. Amides such as fatty acid amides, ethoxylated fatty acid amides, solid fatty acid alkanolamides.

The lotions further comprise from 1% to 10%, preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sufates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably substituted phenylacetic acid amide is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite.

2. Creams

Compositions of this invention also can be formulated in a cream form. The creams comprise an effective amount of the substitued phenylacetic acid amide; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The compositions of this invention can be also formulated in a solution form. The solution form comprises an effective amount of the substitued phenylacetic acid amide; the balance being a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions in the solution form can be applied to the skin as is, or else can be formulated into a aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Compositions herein can be formulated into a gel form by simply admixing a suitable thickening agent to the previously described solution compositions. Examples of suitable thickening agents have been previously described with respect to the lotions.

The gelled compositions comprise an effective amount of the substituted phenylacetic acid amide, from 5% to 75%, preferably from 10% to 50%, of an organic solvent as previously described; from 0.5% to 20%, preferably from 1% to 10% of the thickening agent; the balance being water.

5. Solids

The compositions of this invention can also be formulated into a solid form. Such forms have use as a stick-type composition intended for application to the lips or other part of the body. Such compositions comprise an effective amount of the substituted phenylacetic acid amide and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

Additives commonly found in topical compositions such as preservatives, e.g., methyl and ethyl-paraben, dyes and perfume can be included in any of the previously described compositions.

The substituted phenylacetic acid amides of the present invention are also useful when used systemically, for example by parenteral administration. The dosage of the substituted phenylacetic acid amide which is both safe and effective to provide analgesic or anti-irritant activity will vary with the particular condition being treated, the severity of the condition, the duration of treatment, the specific substituted phenylacetic acid amide employed and its usage concentration, and like factors within the specific knowledge and expertise of the attending physician and commensurate with a reasonable benefit/risk ratio associated with the use of any drug compound. The systemic dosages and dosage ranges given herein are based on delivery of the substituted phenylacetic acid amide to a 70 kg human and can be adjusted to provide equivalent dosages for patients of different body weights.

For mammals, especially humans, total single dosages from 0.5 mg to 10 g are acceptable. Total single dosages from 100 mg to 5 g are preferred. While dosages higher than the foregoing are effective, toxicity and side effects may present problems in some individuals.

The substituted phenylacetic acid amides can be administered parenterally in combination with a pharmaceutically-acceptable carrier such as corn oil, Cremophor EL or sterile, or pyrogen-free water and a water-miscible solvent (e.g., ethyl alcohol) at a practical amount of the substituted phenylacetic acid amide per dose. Parenteral administration can be by subcutaneous, intradermal, intramuscular, intraarticular, or intravenous injection. The single dosage by these modes of administration is usually in the range of from about 0.1 mg to about 10 g per day. Obviously, multiple dosages will exceed this amount depending upon such factors as length of treatment and the severity of the condition being treated.

As used herein the term "pharmaceutically-acceptable carrier" denotes a solid or liquid filler, diluent, or encapsulating substance. Such examples of substances which can serve as pharmaceutical carriers for substituted phenylacetic acid amides include: sugars, such as lactose, glucose and sucrose; starches, such as corn starch and potato starch; cellulose and its derivatives, such as sodium carboxymethylcellulose, ethyl cellulose, cellulose acetate, powdered tragacanth; malt; gelatin; talc; stearic acid magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as the Tweens ®, as well as other non-toxic compatible substances typically used on pharmaceutical formulations. Wetting agents and lubricants, such as sodium lauryl sulfate, as well as coloring agents, and preservatives, can also be present.

The pharmaceutical carrier employed in conjunction with the substituted phenylacetic acid amide is used at a concentration sufficient to provide a practical size to dosage relationship. Preferably, the pharmaceutical carrier comprises at least about 98% by weight of the total composition.

Specific oral, topical, and systemic formulations useful in this invention are described in the following U.S. Pat. Nos., all incorporated by reference herein: U.S. Pat. No. 4,401,663, Buckwalter, et al, issued Aug. 30, 1983; U.S. Pat. No. 4,424,205, LaHann, et al, issued Jan. 31, 1984; U.S. Pat. No. 4,443,473, Buckwalter, et al, issued Apr. 12, 1984; U.S. Pat. No. 4,493,848, LaHann, et al, issued Jan. 15, 1984.

Methods for Producing Anti-Inflammatory Activity and Analgesia

The present invention also encompasses methods of producing anti-inflammatory activity and analgesia in humans or lower animals through administering, to the human or lower animal, a safe and effective amount, usually from about 0.1 mg/kg to about 500 mg/kg per day, preferably from about 1 mg/kg to about 100 mg/kg per day, of a substituted phenylacetic acid amide described herein. This amount can be given in a single dose or multiple doses repeatedly over the course of the treatment. While dosages higher than the foregoing are effective to reduce inflammation and produce analgesia, care must be taken in some individuals to prevent adverse side effects. The substituted phenylacetic acid amides and compositions of this invention can be used to treat and prevent pain, to provide analgesia, and to reduce inflammation in various disorders at the deeper structures, muscles, tendons, bursa and joints associated with disease and trauma, and in various other conditions in which non-steroidal anti-inflammatory, antipyretic and analgesic drugs, such as aspirin, and opioids, such as morphine, have heretofore been used to alleviate pain and discomfort and reduce inflammation.

The substituted phenylacetic acid amide and compositions of the instant invention can be administered topically, orally, or systemically.

Topical administration can be used to reduce inflammation and produce local or systemic analgesia, through directly laying on or spreading a safe and effective amount of the substituted phenylacetic acid amide, or composition containing a substituted phenylacetic acid amide, on epidermal or epithelial tissue, including outer skin and oral, gingival, and nasal tissue. The amount of the pharmaceutical composition to be topically administered may vary from about 1 mg/cm$^2$ to 5 mg/cm$^2$, and if a patch is worn over the affected area possibly higher concentrations, depending upon such factors as the sensitivity, type and location of tissue to be treated, the composition and carrier (if any) to be administered, and the particular substituted phenylacetic acid amide to be administered as well as the particular disorder to be treated and the extent to which systemic (as distinguished from local) effects are desired. The extent of systemic analgesia also depends upon such factors as the amount of substituted phenylacetic acid amide, the area of tissue to be covered, and the ability of the phenylacetic acid amide to penetrate the skin tissue.

Oral administration can be used to reduce inflammation and produce analgesia through oral dosing of a pharmaceutical composition comprised of a safe and effective amount of the substituted phenylacetic acid amide of the present invention in a suitable oral pharmaceutical carrier. The substituted phenylacetic acid amide is absorbed by the gastrointestinal tract. The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

The amount of the substituted phenylacetic acid amide ingested depends upon the bioavailability of the compound from the oral pharmaceutical composition. The amount of the pharmaceutical composition depends upon the percent of substituted phenylacetic aqcid amide within its formula, which is a function of the amount of the substituted phenylacetic acid amide required per dose, its stability, release characteristics and other pharmaceutical parameters.

Generally, the oral pharmaceutical composition should comprise from about 5% to about 50% of the substituted phenylacetic acid amide. Systemic administration can also be used to reduce inflammation and produce analgesia. Such administration may be intravenously, intramuscularly, or subcutaneously. The amount of pharmaceutical composition typically administered may vary from about 0.5 to about 5 ml of a solution or suspension of the substituted phenylacetic acid amide in a pharmaceutically-acceptable carrier in a single dose. These compositions may also be administered systemically in multiple dosages, or by infusion.

The following non-limiting Examples illustrate the compounds, compositions, and methods of treatment of the present invention.

EXAMPLE I

N-oleyl-4 hydroxy-3-methoxyphenylacetamide was synthesized by the following method:

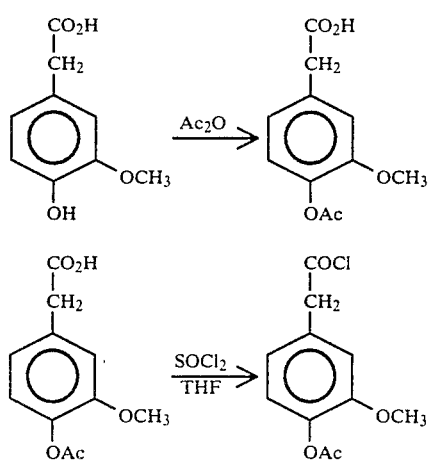

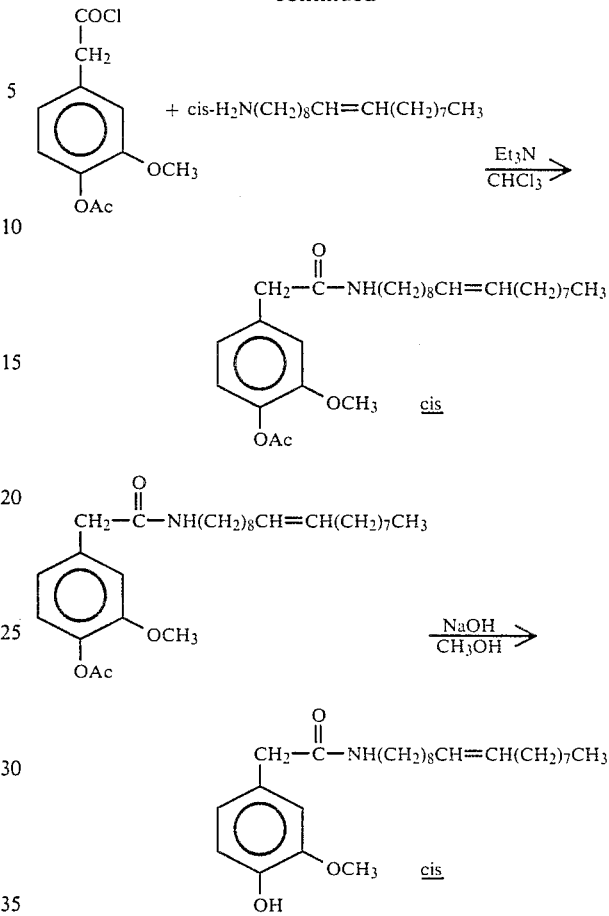

Specifically, acetic anhydride (120 mL) was added to 30.0 g (165 mmol) homovanillic acid and the mixture was allowed to reflux for 6 hours. The solvent was evaporated, leaving an oil which was poured into 1L $H_2O$ and allowed to stir overnight. The solid was collected and dried in vacuo to give 33.1 g of 4-acetoxy-3-methoxyphenylacetic acid.

A solution of 32.7 g of 4-acetoxy-3-methoxyphenylacetic acid (146 mmol), 200 mL THF, and 40 mL $SOCl_2$ was allowed to reflux for 4 hours. The solvent was evaporated to give a crude oil (60 g) of 4-acetoxy-3-methoxyphenylacetyl chloride which was used without further purification.

A mixture of 43.0 g (161 mmol) oleylamine, 14.8 g (146 mmol) $Et_3N$, and 500 mL petroleum ether was added dropwise to a solution of the crude oil (60 g) and 500 mL $CH_2Cl_2$ at 0° C. After addition was complete the mixture was allowed to stir at room temperature overnight. The reaction was poured into 500 mL aqueous 10% HCl. The emulsion which formed was eliminated by additional $H_2O$ and $CH_2Cl_2$. The layers were separated and the $H_2O$ layer was washed with 5×200 mL $CH_2Cl_2$. The combined organics were washed with 250 mL $H_2O$, 500 mL saturated NaCl, and dried over $MgSO_4$. Evaporation gave 90 g of N-oleyl-4-acetoxy-3-methoxyphenylacetamide as an oil.

A solution of 13.2 g (300 mmol) NaOH in 82 mL $H_2O$ was added dropwise to a stirred solution of the crude oil of N-oleyl-4-acetoxy-3-methoxyphenylacetamide in 500 mL MeOH. After 3 hours a thin layer chromatography (TLC) analysis indicated the presence of unreacted starting material. An additional 3.3 g NaOH (82.5 mmol) in 10 mL H₂O was added dropwise to the stirred solution. After 0.5 hours a TLC analysis showed complete consumption of starting material. The solution was acidified at 0° C. to pH=2 with conc. HCl, and the

EXAMPLE III

N-2-Octyl-2-(4-hydroxy-3-methoxyphenyl)-propionamide was synthesized by the following method:

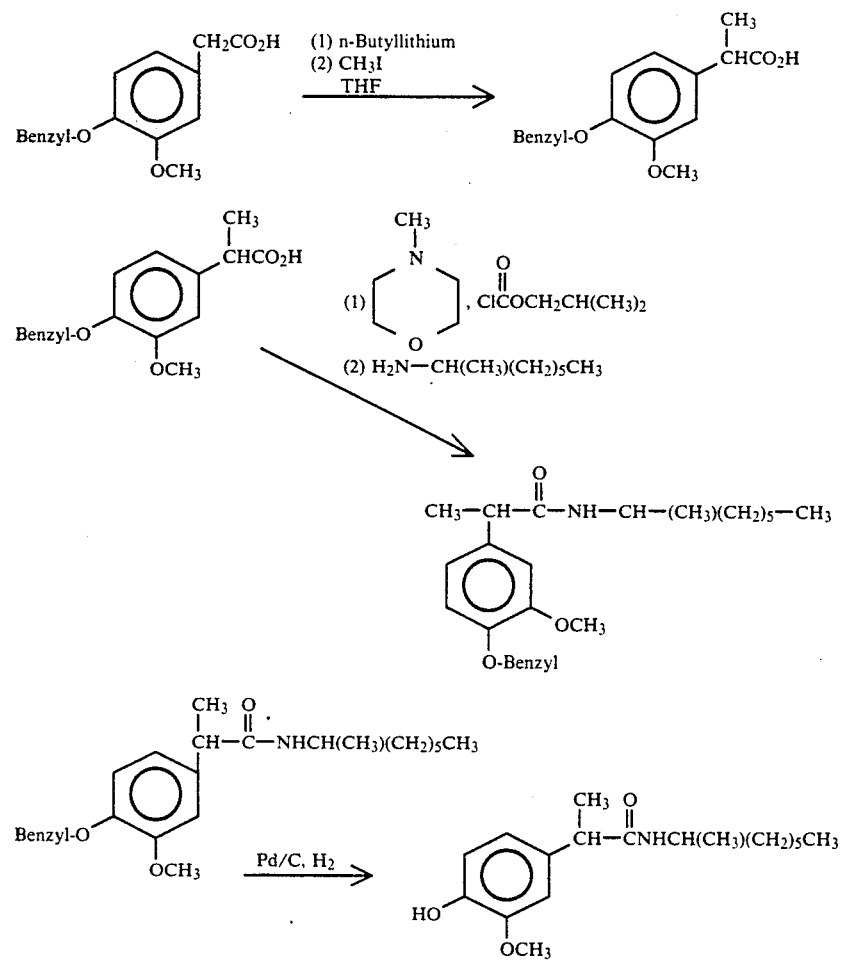

solvent was evaporated. To the residue was added 500 mL CHCl₃ and 500 mL H₂O, and the mixture was stirred for 5 minutes. The layers were separated and the water layer was extracted with 2×200 mL CHCl₃. The combined organics were washed with 100 mL saturated NaHCO₃, 100 mL H₂O, and 2×100 mL saturated NaCl, and dried over MgSO₄. Solvent evaporation gave 71 g of a brown oil which was chromatographed on 1.5 kg SiO₂ using CHCl₃ and later 5% EtOH/CHCl₃ as eluants. Fractions containing the desired spot were collected to give 22.4 g of N-oleyl-4-hydroxy-3-methoxyphenylacetamide. This material was twice more purified by chromatography on 400 g SiO₂, using petroleum ether/CHCl₃ mixtures as eluant, collecting only the most pure fractions to give 11.5 g of N-oleyl-4-hydroxy-3-methoxyphenylacetamide as a broad-melting wax which would not solidify. The wax and mother liquor were combined and recrystallized from 60 mL of Et₂O and 1 L of pentane (collected at room temperature) to give 5.9 g of N-oleyl-4-hydroxy-3-methoxyphenylacetamide as a white, free-flowing, waxy powder.

EXAMPLE II

N-elaidyl-4-hydroxy-3-methoxyphenylacetamide was synthesized as above in Example I except that elaidyl amine was substituted for oleyl amine.

This process led to the formation of separable, racemic diasteromeric substituted phenylacetic acid amides.

Specifically, a solution of 2-(4-benzyloxy-3-methoxyphenyl) acetic acid 15.0 g, 55.1 mmoles) in dry THF (350 mL) was cooled to −78° C. under argon and treated dropwise with n-butyllithium (42 mL, 2.6M in hexanes). The yellow suspension was then allowed to warm to −10° C. and stirred for 60 minutes. A solution of methyl iodide (3.9 mL, 62.6 mmoles) in THF (15 mL total solution) was then added dropwise via syringe over 30 min resulting in a now homogeneous and clear solution. After 2 hours the THF was rotary evaporated and the residue was dissolved in ethyl acetate (500 mL), extracted with 10% phosphoric acid (3×100 mL), extracted with brine (1×100 mL) and dried over magnesium sulfate. Rotary evaporation afforded a yellow oil which solidified on standing. The solid was triturated with n-pentane and filtered to give 2-(4-benzyloxy-3-methoxyphenyl)propionic acid (14.0 g, 89%) as a yellow powder.

A solution of 2-(4-benzyloxy-3-methoxyphenyl)propionic acid (5.0 g, 17.5 mmoles) and 4-methylmorpholine (2.0 mL, 17.5 mmoles) in ethyl acetate (170 mL) at 0° C. was treated with isobutyl chloroformate (2.26 mL, 17.5 mmoles). The resulting white slurry was stirred for 20 minutes. A solution of racemic 2-octylamine (2.7 g, 21 mmoles) in ethyl acetate (10 mL total solution) was added to the suspension which was then stirred for 3 hours. The mixture was extracted with 1M hydrochloric acid (3×50 mL), with a saturated sodium bicarbonate solution (3×50 mL), with brine (1×50 mL) and dried over magnesium sulfate. The ethyl acetate was rotary evaporated affording N-2-octyl-2-(4-benzyloxy-3-methoxyphenyl)proprionamide as a white solid which was crystallized from ether/methylene chloride to give 4.55 g. This racemic mixture of diastereomers was separated by silica gel chromatography.

A solution of N-2-octyl-2-(4-benzyloxy-3-methoxyphenyl) proprionamide in methanol (75 mL) was treated with 5% Pd/C then hydrogenated at room temperature and 50 psig for 4 hours. The solution was filtered through celite to remove the catalyst and evaporated to a residue which was crystallized from chloroform/n-pentane affording the desired amide.

EXAMPLE IV

A composition for oral administration is prepared by combining the following ingredients:
N-oleyl-4-hydroxy-3-methoxyphenylacetamide, 1.10 kg
Sesame oil, 6.50 liters
The methoxyphenylacetamide is dissolved in the sesame oil with the aid of sonication and is packaged in soft gelatin capsules using methods known in the art. Two of the resulting capsules, each containing 225 mg of the composition, are administered to a 60 kg human in need of treatment, producing analgesia and reducing inflammation.

A substantially similar reduction of inflammation and an increased analgesic effect is obtained when the N-oleyl-4-hydroxy-3-methoxyphenylacetamide is replaced with N-(9-methylene-1-octadecanyl-)-4-hydroxy-3-methoxyphenyl acetamide.

EXAMPLE V

A composition for oral administration is prepared by combining the following ingredients:
N-oleyl-4-hydroxy-3-methoxyphenylacetamide, 250 g
Propylene glycol, 1800 ml
Ethyl alcohol, 175 ml
Distilled water, 75 ml
Artificial Cherry flavor, 10 ml
FD&C Red #40, 0.2 g
The above ingredients are combined to produce a syrup and are packaged under sterile conditions in 6 oz. bottles. One teaspoon of this formulation is administered to a 70 kg adult human, reducing inflammation and producing analgesia.

A substantially similar reduction of inflammation, but a weaker analgesic effect, is obtained when the N-oleyl-4-hydroxy-3-methoxyphenylacetamide is replaced with N-cyclooctyl-4-hydroxy-3-methoxyphenylacetamide.

EXAMPLE VI

A composition for topical administration is prepared by combining the following ingredients:
N-oleyl-4-hydroxy-3-methoxyphenylacetamide, 4 g
Propylene glycol, 100 ml
Ethyl alcohol, 100 ml
The phenylacetamide is melted with slight warming and combined with the other ingredients. Application of 0.4 ml of the resulting liquid to a 80 cm² portion of the forearm of a 60 kg human reduces inflammation and produces analgesia.

A substantially similar reduction of inflammation, but a weaker analgesic effect, is obtained when the N-oleyl-4-hydroxy-3-methoxyphenylacetamide is replaced with N-stearyl-4-hydroxy-3-methoxyphenylacetamide.

Effectiveness in Reducing Inflammation and Providing Analgesia

EXAMPLE VII

Substituted phenylacetic acid amide compounds were tested for anti-inflammatory activity using the Carrageenan Rat Paw Edema Test (Oil Vehicle).

Male Sprague Dawley rats (Charles River Laboratories) were weighed and food fasted overnight. The animals were divided into four to six groups of six animals each according to body weights, average about 145 g, so that each group had about the same average weight (within 10 g).

The following morning five ml of water was dosed orally via stomach tube to each animal to facilitate paw swelling. The animals were dosed with the test compound and then placed in individual cages. The drug was dissolved in ethyl oleate: benzyl alcohol, 98:2, and delivered via stomach tube in 1 ml volume.

Paw volumes (0 time) were determined on both hind paws with a mercury displacement device equipped with a transducer and digitizer. One hour after dosing the test compound, the animals were placed in a plastic restrainer and 50 l of a 1% (w/w) carrageenan solution in 0.9% saline was injected into the ventral surface of the left rear paw. Four hours after the carrageenan injection, the paw volumes are again determined.

The results are expressed as percent inhibition of the mean paw volume of the test group relative to the control group according to the formula:

$$(C-T a..n)/C \times 100 = \text{Percent Inhibition}$$

where C is the average difference in paw volume before and after carrageenan-induced swelling and Ta..n is the difference in paw swelling in the treated animals (a..n). Statistical differences are determined by one way analysis of variance.

| Compound | Dose | Percent Inhibition |
|---|---|---|
| N-oleyl-4-hydroxy-3-methoxyphenyl acetamide | 200 mg/kg | 89.3 +/− 10.8 |
| | 400 mg/kg | 95.6 +/− 11.2 |

All values significant p 0.05

EXAMPLE VIII

Substituted phenylacetic acid amide compounds were tested for anti-inflammatory activity using the Croton Oil Inflamed Mouse Ear Test (Topical treatment).

Adult male Cox ICR mice, 25–35 g, were treated at about 3:00 PM on the left ear with 25 l of a 1% solution of the test compound in ethanol. They were placed in individual stainless steel cages where food and water was available ad libitum. The following morning around 8:00 AM the mice were dosed a second time on the same ear. One hour after the second dose, 25 l of 2% croton oil in acetone was applied to the left ear of the control and test groups.

Four hours after the croton oil treatment, the mice were sacrificed by cervical dislocation and both ears removed. A 5 mm punch biopsy was taken from each ear and weighed to the nearest 0.1 mg on a Cahn electrobalance.

The results were expressed as percent inhibition of the swelling response compared to the control group according to the formula:

$$(C - Ta..n)/C \times 100 = \text{Percent Inhibition}$$

where C is the average difference between the left and right ear weights of the control group, and Ta..n is the difference between left and right ear weights of animal (a..n) in a treated group.

Statistical tests for significance between groups were made using a one way analysis of variance of the ear weight differences.

| Compound | Percent Inhibition |
| --- | --- |
| N-9-decenyl-4-hydroxy-3-methoxyphenylacetamide | 98.9 +/− 11.9 |
| N-octyl-4-hydroxy-3-methoxyphenylacetamide | 89.1 +/− 15.7 |
| N-octyl-4-hydroxy-3-methoxyphenyl-2-methyl-acetamide | 88.9 +/− 24.1 |
| N-oleyl-4-hydroxy-3-methoxyphenylacetamide | 83.5 +/− 11.9 |
| N-nonyl-4-hydroxy-3-methoxyphenylacetamide | 80.7 +/− 23.0 |
| N-heptyl-4-hydroxy-3-methoxyphenylacetamide | 69.4 +/− 33.9 |
| N-decyl-4-hydroxy-3-methoxyphenylacetamide | 58.1 +/− 29.4 |
| N-(2-nonanyl)-4-hydroxy-3-methoxyphenylacetamide | 55.6 +/− 26.5 |
| N-dodecyl-4-hydroxy-3-methoxyphenylacetamide | 55.3 +/− 20.7 |
| N-(2-octanyl-)-4-hydroxy-3-methoxyphenylacetamide | 48.1 +/− 15.8 |

All values significant p 0.05

Rodent Hot Plate Test

The degree of thermal analgesia obtained was determined using the "rodent hot plate test" (RHP). The RHP system was designed to detect and evaluate agents which elevate the threshold for the perception of pain. Classically, this method has been utilized primarily to evaluate opioid (narcotic) analgesic agents, such as morphine. Unless administered in toxic quantities, antipyretic analgesics, such as aspirin or acetaminophen, exhibit little or no activity in the RHP system.

Groups of 8 male CF-1 male or 8 male Sprague-Dawley rats were used to evaluate each composition. The test procedure consisted of placing a particular rodent on a surface heated to 55° C. and observing its behavior. The point in time at which the rodent either rapidly fanned one of its rear paws or licked a hind paw was noted, and the total elapsed time from the first contact with the heated surface was determined ("response time"). If the response time for a particular rodent reached sixty seconds, the rodent was removed from the hot plate so as to prevent organic damage, and the response time recorded as sixty seconds. Hence, the maximum measurable response time for any particular composition was sixty seconds.

EXAMPLE IX

An analgesic composition for oral administration was made with the following ingredients:
Sesame oil, 50 ml
Substituted phenylacetic acid, 300 mg The substituted phenylacetic acid amide was dissolved in the sesame oil by heating and sonication. The resulting dosing solution was administered using 5 ml/kg body weight to 8 Sprague-Dawley rats. The analgesic activity was then measured using the RHP test described above and compared against the analgesic activity of morphine.

| Drug | Response time, Sec. +/− 5.0 sec. |
| --- | --- |
| Vehicle (saline) | 4.9 |
| Morphine (20 mg/kg) | 59.8 |
| Vehicle (sesame oil) | 7.7 |
| Subsituted phenylacetic acid amide (150 mg/kg) | 53.6 |

What is claimed is:

1. A substituted phenylacetic acid amide compound, and pharmaceutically-acceptable salts thereof, of the formula:

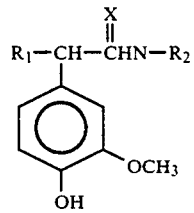

wherein X is O or S; $R_1$ is H, OH or $CH_3$; $R_2$ is monounsaturated straight chain alkenyl having from 14 to about 20 carbon atoms.

2. The compound of claim 1 wherein $R_1$ is H or $CH_3$.
3. The compound of claim 2 wherein $R_1$ is H.
4. The compound of claim 1 wherein X is O.
5. The compound of claim 3 wherein X is O.
6. The compound of any of claims 1–5 wherein $R_2$ is selected from the group consisting of 9E-tetradecenyl, 9Z-tetradecenyl, 9E-hexadecenyl, 9Z-hexadecenyl, 9E-octadecenyl, 9Z-octadecenyl, 6E-octadecenyl, 6Z-octadecenyl, 11E-octadecenyl, 11Z-octadecenyl, 10E-nonadecenyl, 10Z-nonadecenyl, 13E-docosenyl and 13Z-docosenyl.
7. The compound of claim 1 selected from the group consisting of N-oleyl-4-hydroxy-3-methoxy-phenylacetamide and the pharmaceutically-acceptable salts thereof.
8. A pharmaceutical composition for reducing inflammation and producing analgesia in humans or animals comprising:
(a) a safe and effective amount of a substituted phenylacetic acid amide compound, or a pharmaceutically-acceptable salt thereof, of the formula:

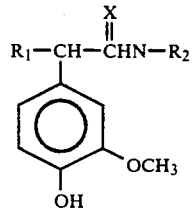

wherein X is O or S; $R_1$ is H, OH or $CH_3$; $R_2$ is monounsaturated straight chain alkenyl having from 14 to about 20 carbon atoms; and
(b) a pharmaceutically-acceptable carrier.

9. The composition of claim 8 wherein the substituted phenylacetic acid amide compound comprises from about 1% to about 95% of the total composition.

10. The composition of claim 9 wherein $R_1$ is H or $CH_3$.

11. The composition of claim 10 wherein $R_1$ is H.

12. The composition of claim 9 wherein X is O.

13. The composition of claim 11 wherein X is O.

14. The composition of any of claims 9, 11 and 13 wherein $R_2$ is selected from the group consisting of 9E-tetradecenyl, 9Z-tetradecenyl, 9E-hexadecenyl, 9Z-hexadecenyl, 9E-octadecenyl, 9Z-octadecenyl, 6E-octadecenyl, 6Z-octadecenyl, 11E-octadecenyl, 11Z-octadecenyl, 10E-nonadecenyl, 10Z-nonadecenyl, 13E-docosenyl and 13Z-docosenyl.

15. The composition of claim 9 wherein the substituted phenylacetic acid amide is selected from the group consisting of N-oleyl-4-hydroxy-3-methoxyphenyl acid amide and the pharmaceutically-acceptable salts thereof.

* * * * *